(12) United States Patent
Nguyen et al.

(10) Patent No.: US 8,309,736 B2
(45) Date of Patent: Nov. 13, 2012

(54) ALKYL H-PHOSPHONATES OF N,N'-DIALKYLIMIDAZOLIUMS AND OF QUATERNARY AMMONIUMS AND USES THEREOF

(75) Inventors: Hoang-Phuong Nguyen, Toulouse (FR); Michel Baboulene, Toulouse (FR)

(73) Assignees: Centre National de la Recherche Scientifique (CNRS), Paris (FR); Universite Paul Sabatier Toulouse III, Toulouse (FR)

( * ) Notice: Subject to any disclaimer, the term of this patent is extended or adjusted under 35 U.S.C. 154(b) by 526 days.

(21) Appl. No.: 12/527,163

(22) PCT Filed: Feb. 15, 2008

(86) PCT No.: PCT/EP2008/051898
§ 371 (c)(1),
(2), (4) Date: Aug. 13, 2009

(87) PCT Pub. No.: WO2008/101881
PCT Pub. Date: Aug. 28, 2008

(65) Prior Publication Data
US 2010/0121075 A1 May 13, 2010

(30) Foreign Application Priority Data
Feb. 16, 2007 (FR) ..................... 07 53321

(51) Int. Cl.
*C07C 211/63* (2006.01)
*C07D 233/56* (2006.01)
*C07D 239/26* (2006.01)
(52) U.S. Cl. ....................... 546/347; 548/335.1; 564/281
(58) Field of Classification Search .................. None
See application file for complete search history.

(56) References Cited

U.S. PATENT DOCUMENTS

| | | | |
|---|---|---|---|
| 1,943,176 | A | 1/1934 | Graenacher et al. |
| 2,815,345 | A | 12/1957 | Zech |
| 4,045,414 | A | 8/1977 | Rabilloud et al. |
| 4,045,519 | A | 8/1977 | Wright |
| 4,064,176 | A | 12/1977 | Rabilloud et al. |
| 4,116,788 | A | 9/1978 | Schmitt et al. |
| 4,139,616 | A | 2/1979 | Ducret et al. |
| 4,143,059 | A | 3/1979 | Abblard et al. |
| 4,147,728 | A | 4/1979 | Rabilloud et al. |
| 5,294,632 | A | 3/1994 | Erion et al. |
| 7,145,004 | B2 | 12/2006 | Ignatyev et al. |
| 2008/0033209 | A1 | 2/2008 | Szarvas et al. |
| 2008/0190321 | A1 | 8/2008 | Maase et al. |

FOREIGN PATENT DOCUMENTS

| | | |
|---|---|---|
| DE | 1078558 B | 3/1960 |
| DE | 2456627 A1 | 6/1975 |
| DE | 2646416 A1 | 5/1977 |
| DE | 10220547 A1 | 11/2003 |
| FR | 2370750 A1 | 6/1978 |
| FR | 2402663 A2 | 4/1979 |
| FR | 2486079 A1 | 1/1982 |
| GB | 1302894 A | 1/1973 |
| JP | 08088146 A | 4/1996 |
| SU | 495319 A1 | 12/1975 |
| WO | WO-03029329 A2 | 4/2003 |
| WO | WO-2006021304 A1 | 3/2006 |
| WO | WO-2007057235 A2 | 5/2007 |

OTHER PUBLICATIONS

Zwierzak et al.; 'Organophosphorus Esters-IV, Novel Approach to Monoalkyl Hydrogen Phosphites', 1973, 29, 1089-1094.
Mikolajczyk et al.; '$^1$H, $^{31}$P, and $^{13}$C Nuclear Magnetic Resonance Nonequivalence of Diastereomeric Salts of Chiral Phosphorus Thio Acids with Optically Active Amines, A Method for Determining the Optical Purity and Configuration of Chiral Phosphorus Thio Acids', 1978, 100(22), 7003-7008.
Bodalski et al.; 'Anchimeric Participation of a Methoxy Group in a Reaction of a Metathiophosphate', 1994, 59, 5173-5178.
Kluba et al.; 'Alkylation of Tera-n-butylaminium Alkyl Hydrogen Phosphites, A New Route to Mixed Dialkyl Phosphites', 1978, 134-137.
Mautz et al.; 'Synthesis of 0-Geranyl (I-Thio) Diphosphate', 1989, 30(52), 7333-7336.
Troev et al.; 'A Study of the Atherton—Todd Reaction Mechanism', 1990, 63(4), 1284-1285.
Georgiev et al.; 'Conversion of Chlorofluorocarbons into Chlorofluorohydrocarbons Using the Atherton—Todd Reaction with Dimethyl Phosphate', 1992, 31(10), 1965-1968.
Ramirez et al.; '5-Membered Cyclic Acyl Phosphates, A New Class of Extremely Reactive Phosphorylating Agents', 1973, 29(23), 3741-3753.
Sobanov et al.; 'Kinetics and Mechanism of the Pudovik Reaction in the Azomethine Series: III. Acid-catalyzed Hydrophosphorylation of Imines', 2006, 76(3), 421-429.
Georgiev et al.; 'Studies on the Stabilities of Alkylmethylammonium Salts of Monomethyl Esters of Phosphonic Acids', 1994, 88(1-4), 139-145.
Kluba et al.; 'Organophosphorus Esters. Part V., Attempted Application of Benzyl As Protecting Group in Phosphorylation of Alkyl Halides', 1974, 48(2), 277-286.
Ilia et al.; 'Synthesis of Mixed Alkylphosphites and Alkylphosphates', 2003, 178(7), 1513-1519.
Vepsalainen et al.; 'Bisphosphonic Compunds. IV. Preparation and Identification of Mixed Tetraalkyl Methylene and (Dichloromethylene)- Bisphosphonates by NMR Spectroscopic, Mass Spectrometric and X-Ray Crystallographic Studies', 1992, 70(3-4), 183-203.
Troev et al.; 'Hofmann Elimination Reaction with Phosphorus Containing Alkylammonium Salts', 1988, 37(3-4), 243-245.
Troev et al.; 'Structures of Phosphorus-Containing Metal and Ammonium Salts', 1988, 36(3-4), 189-195.

(Continued)

Primary Examiner — Michael Barker
(74) Attorney, Agent, or Firm — Harness, Dickey & Pierce, P.L.C.

(57) ABSTRACT

The application relates to the use of a salt associating an ammonium cation with an alkyl H-phosphonate anion of the following formula (I) in which R is a hydrocarbon radical, the pointed bond can be present or not, the radical $R_3$ being then present or absent, as an ionic liquid. The ammonium cation is preferably an imidazolium cation. This ionic liquid is particularly useful in the field of green chemistry as a substitute for organic solvents. The application also relates to a method for preparing such a salt by the direct dealkylation of the corresponding dialkylphosphite by the appropriate nitrated base, in one step and without any solvent. The application also relates to a method for preparing mixed methylated phosphites.

17 Claims, No Drawings

OTHER PUBLICATIONS

Kluba et al., 'Proby Syntezy Peotydow Na Drodze Reakcji Rittera', 1973, 27, 159-160.

Troev et al.; 'Review Characteristic Reactions of the Alkoxy Groups of the Acid Diesters of Phosphorous Acid', 1987, 29, 129-146.

Sang-gi Lee; 'Functionalized Imidazolium Salts for Task-Specific Ionic Liquids and Their Applications', 2006, 1049.

Swatloski R.P.; 'Dissolution of Cellose with Ionic Liquids', 2002, 124, 4974-4975.

Zhang H. et al.; '1-Allyl-3-Methylimidazolium Chloride Room Temperature Ionic Liquid: A New and Powerful Nonderivatizing Solvent for Cellulose', 2005, 38, 8272-8277.

Fukawa Y. et al.; 'Superior Solubility of Polysaccharides in Low Viscosity, Polar, and Halogen-Free 1,3-Dialkylimidazolium Formates', 2006, 7, 3295-3298.

Kers A. et al.; 'Studies on Aryl H-Phosphonates; Part 2: A General Method for the Preparation of Alkyl H-Phosphonate Monoesters', 1995, 427-430.

Ford-Moore et al.; 'Triethyl Phosphite', vol. IV, p. 955 [Organic Syntheses, Coll.,4:955 (1963)].

Cook et al.; 'Esters Containing Phosphorus. Part VIII. Structural Requirements for High Toxicity and Miotic Action of Esters of Fluorophosphionic Acid', 1949, 635.

Fukaya et al.; 'Cellulose Dissolution with Polar Ionic Liquids Under Mild Conditions: Required Factors for Anions', 2008, 10, 44-46.

Liu Q. et al.; 'Room Temperature Ionic Liquids that Dissolve Carbohydrates in High Concentrations', 2005, 7, 39-42.

Forsyth S. et al.; 'Rapid, Clean, and Mild O-Acetylation of Alcohols and Carbohydrates in an Ionic Liquid', 2002, 714-715.

ALKYL H-PHOSPHONATES OF N,N'-DIALKYLIMIDAZOLIUMS AND OF QUATERNARY AMMONIUMS AND USES THEREOF

CROSS-REFERENCE TO RELATED APPLICATIONS

This application is a National Phase Entry of International Application No. PCT/EP2008/051898, filed on Feb. 15, 2008, which claims priority to French Patent Application No. 0753321, filed on Feb. 16, 2007, both of which are incorporated by reference herein.

BACKGROUND AND SUMMARY

The invention relates to the use of salts associating an ammonium cation with an alkyl H-phosphonate anion, as ionic liquids. In particular these salts are liquid at room temperature.

Ionic liquids are organic salts having melting points below 100° C. and often even below room temperature. They are increasingly used as substitutes for traditional organic solvents in chemical reactions. The most common of them consist in imidazolium or pyridinium cations but they may also consist in phosphonium or tetraalkyl ammonium cation:

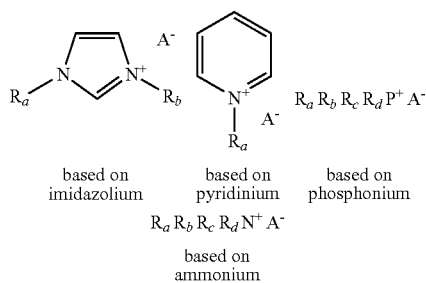

based on imidazolium    based on pyridinium    based on phosphonium $R_a R_b R_c R_d N^+ A^-$ based on ammonium The radicals $R_a$-$R_b$ are advantageously selected independently of each other from a hydrogen atom and $C_1$-$C_6$ alkyls. The anion $A^-$ may notably be selected from a halide ($Cl^-$, $Br^-$, $F^-$, $I^-$), $PF_6^-$, $BF_4^-$, $CF_3CO_2^-$, $CF_3SO_3^-$, $(CF_3SO_3)_2N^-$, $CN^-$, $SCN^-$, $(CN)_2N^-$, $FeCl_4^-$, and $SbF_6^-$.

Ionic liquids have very good dissolution properties for most organic and inorganic compounds. They generally have the following properties:
  they are stable at high temperature,
  they have a quasi-zero vapor pressure,
  they are non-flammable (except for a whole class of ionic liquids, so-called "energetic" liquids, consisting of nitrate or picrate anions, for example).

Physical studies (infrared, Raman, neutron diffraction, nuclear magnetic resonance, X-ray diffraction), as well as theoretical calculations (molecular dynamics), have shown that ionic liquids have pronounced self-organization. Although these are liquids, they have a "glassy" character, and have heterogeneities at a microscopic scale (at a scale of ~0.1 nm). One encounters highly polar regions (comparable to water) as well as apolar regions (comparable with organic solvents). On the other hand, this organization explains the ionic conductivity of these solvents and justifies their use as an electrolyte.

The main applications of ionic liquids are the following
  as solvents in synthesis and catalysis reactions, for example Diets-Alder cycloaddition reaction, Friedel-Crafts alkylation, hydrogenation, hydroformylation, oxidation reactions or Heck's reactions;
  as substitutes for traditional organic solvents in biphasic systems involved in separation and extraction processes;
  as electrolytes in electrochemistry;
  as a solvent in the synthesis of materials, and more particularly of nanostructured materials: mesoporous oxides, metal nanoparticles or anisotropic particles (nanosheets or nanorods).

Their heat stability, their non-flammable and non-volatile character make them solvents for the future in industrial processes. Moreover, the rate of the reactions, the selectivity and the yield are often better in ionic liquids. Their non-volatility is exploited in many chemical processes.

Further, aware from environmental problems, chemists have to turn towards safer less polluting methods. The massive use of volatile organic solvents causes involvement of the chemical industry in rejecting green house effect gases. New orientations have therefore arisen through the name of "green chemistry". Consequently, substitution of conventional solvents has experienced great development notably with ionic liquids. Essentially, they are grouped in four large families: $AlCl_3$ (Lewis acid), ammonium, phosphonium, and pyridinium salts. Their fields of applications gradually widen over the years and practically all the industrial sectors show interest for the latter. The increase in scientific literature on ionic liquids is considerable.

Well-known for several years under the name of molten salts, it is only recently that the name of ionic liquids (IL) is used especially with the arrival of green chemistry. In connection with the particularities of their physico-chemical properties: a melting point below 100° C., quasi-zero vapor pressure, heat stability, recyclable solvent, these ionic liquids are of increasing interest in all industrial fields. They are especially developed in the form of solvents as a substitution for conventional organic solvents in accordance with present environmental considerations. Their chemical structure, an association of a cation and of an anion, gives free expression to the imagination of chemists, which explains the increasing number of commercial ionic liquids. Generally, ionic liquids based on ammonium (optionally substituted with alkyl radicals) are prepared in two steps: quaternization of an amine by a halogenated derivative (first type of ionic liquids), followed by metathesis by exchange of the halide anion by the appropriate anion such as $PF_6^-$, $BF_4^-$, $(CN)_2N^-$, $(CF_3SO_2)_2N^-$, etc. (second type of ionic liquids). The major drawback of this method lies in obtaining ionic liquids either with a melting point above 30° C. ($1^{st}$ type) or by the presence of fluorine or of the CN function, which are degraded into toxic or corrosive products ($2^{nd}$ type).

In this context, the inventors have contemplated a new category of salts associating an ammonium with an alkyl H-phosphonate anion (also called an alkoxy H-phosphonate, alkyl phosphonate or monoalkyl phosphite), which are used as ionic liquids. Their syntheses are simple and inexpensive. The physical characteristics of some of these salts, liquid at room temperature, make them very competitive on the vast market of ionic liquids. Conventional chemical reactions transposed in these ionic liquids show a positive effect of the latter, either on the rate of reaction or on an improvement in the yields, or a lowering of the costs with recycled ionic liquids, or by an original reaction orientation leading to unexpected compounds. Surprisingly, the inventors have developed a novel simple synthesis method (in a single reaction step) and respectful of the environment (conducted in the absence of organic solvents) leading to novel salts associating an ammonium cation with an alkyl H-phosphonate anion, these salts being used as novel ionic liquids. Moreover, as reaction solvents, these novel ionic liquids provide original potentialities, in particular in the aldolization reaction between an aromatic aldehyde and acetone.

The invention therefore relates to a salt used as an ionic liquid, said salt associating an ammonium cation with an alkyl H-phosphonate anion fitting the following formula I

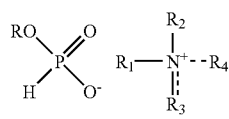

(I)

wherein

R represents a saturated or unsaturated $C_1$-$C_{14}$ hydrocarbon radical, optionally substituted with a function selected from the group constituting of ethers, esters, thioesters and amides;

$R_1$ represents a $C_1$-$C_6$ hydrocarbon radical;

the bond in dotted lines may either be present or not, the radical $R_4$ then being present or absent, if the radical $R_4$ is present, the bond with $R_3$ is a single bond, and $R_2$, $R_3$ and $R_4$ represent independently of each other a $C_1$-$C_6$ hydrocarbon radical or $R_3$ and $R_4$ form together a heterocycloalkyl radical with 5 or 6 members, the heterocycloalkyl radical may have in addition to the nitrogen atom which bears the radicals $R_3$ and $R_4$, one or more hetero-atoms selected from N and O, said heterocycloalkyl radical may be substituted with one or more $C_1$-$C_6$ alkyl radicals and $R_2$ represents a $C_1$-$C_6$ hydrocarbon radical, if the radical $R_4$ is absent, the bond with $R_3$ is a double bond, and $R_2$ and $R_3$ form together a heteroaromatic radical with 5 or 6 members, the said heteroaromatic radical may have, in addition to the nitrogen atom which bears the radicals $R_3$ and $R_4$, one or more hetero-atoms selected from N and O, said heteroaromatic radical may be substituted with one or more $C_1$-$C_6$ alkyl radicals.

Within the scope of the present invention, the hydrocarbon radical may be saturated or unsaturated. It may be with a linear or branched chain. The hydrocarbon radical may contain from 1 to 14 carbon atoms (for the radical R) or from 1 to 6 carbon atoms (for the radicals $R_1$, $R_2$, $R_3$ and $R_4$).

The targeted alkyl radicals in the invention may have a linear or branched chain, they comprise 1 to 6 carbon atoms. As examples of alkyl radicals, mention may notably be made of methyl, ethyl, propyl, isopropyl, butyl and tertiobutyl. Within the scope of the present invention, the term of "heterocycloalkyl" designates a cyclic alkyl group containing in addition to the hydrogen atoms, 5-6 atoms which are the nitrogen atom bearing the radicals ($R_3$ and $R_4$), carbon atoms and optionally an additional hetero-atom selected from N and O. As an example of a heterocycloalkyl radical, mention may notably be made of pyrrolidine, piperidine, and morpholine.

Within the scope of the present invention, the term "heteroaromatic" designates an aromatic radical containing, in addition to the hydrogen atoms, 5-6 atoms which are the nitrogen atom bearing the radical ($R_2$ and $R_3$), carbon atoms and optionally one or more additional hetero-atoms selected from N and O. As an example of a heteroaromatic radical, mention may notably be made of imidazole, pyridine, pyrimidine and pyrazine, and advantageously imidazole, and pyridine. This heteroaromatic radical may itself be substituted with a $C_1$-$C_6$ alkyl radical.

The functional substituents which may be present on the hydrocarbon radical R are:

ether functions, i.e. a radical A-O—B wherein the radical A is absent or represents a linear $C_1$-$C_6$ alkyl radical, and B represents a linear $C_1$-$C_6$ alkyl radical;

oxygen- or sulfur-containing ester (thioester) functions, i.e. a radical A-COX—B, wherein X represents an oxygen or sulfur atom. A and B have the same definition as earlier, amide functions, i.e. a radical A-CO—NH$_2$, wherein A has the same definition as earlier.

The radical $R_1$ advantageously represents a $C_1$-$C_6$ alkyl radical, more advantageously a methyl or ethyl radical.

When the radical $R_4$ is present, the radicals $R_2$, $R_3$ and $R_4$ advantageously each represent independently of each other a $C_1$-$C_6$ alkyl radical, more particularly an ethyl, propyl or butyl radical. Otherwise, the radicals $R_3$ and $R_4$ may advantageously form together a pyrrolidine or morpholine radical and the radical $R_2$ represents a $C_1$-$C_6$ alkyl radical. When the radical $R_4$ is absent, the radicals $R_2$ and $R_3$ advantageously form together a pyridine or imidazole radical, optionally substituted with a $C_1$-$C_6$ alkyl chain.

Preferably, the salt according to the invention is selected from the group constituting of N,N'-dimethylimidazolium methyl H-phosphonate, N,N'-butylmethylimidazolium methyl H-phosphonate, methyltriethylammonium methyl H-phosphonate, methyltributylammonium methyl H-phosphonate, N,N'-ethylmethylimidazolium ethyl H-phosphonate, N,N'-butylethylimidazolium ethyl H-phosphonate, tetraethylammonium ethyl H-phosphonate, N,N'-dimethylimidazolium n-butyl H-phosphonate, N,N'-dimethyl-imidazolium n-hexyl H-phosphonate, N,N'-dimethylimidazolium n-octyl H-phosphonate and N,N'-dimethylimidazolium tetradecyl H-phosphonate. The terms methyl H-phosphonate and methoxyphosphonate are synonyms, as well as the terms ethyl H-phosphonate and ethoxyphosphonate;
butyl H-phosphonate and n-butoxyphosphonate;
hexyl H-phosphonate and hexoxyphosphonate;
octyl H-phosphonate and octoxyphosphonate;
tetradecyl H-phosphonate and tetradecoxyphosphonate.

According to a first advantageous alternative of the invention, the salts of formula I according to the invention are liquid at a temperature below 100° C., and advantageously at room temperature. By "room temperature" is meant a temperature comprised between 20 and 40° C., preferably of about 25° C. Generally, these salts are liquid at room temperature when the radical R represents a saturated or unsaturated $C_1$-$C_4$ hydrocarbon radical, preferably the radical R represents a methyl or ethyl radical. These salts may also be liquid at room temperature when the radical R represents a $C_5$-$C_{14}$ hydrocarbon radical which is unsaturated and/or substituted with a function selected from the group constituting of ethers, esters, thioesters and amides.

Advantageously, the salt according to the invention associates a methyl H-phosphonate or ethyl H-phosphonate anion, with a N,N'-dimethylimidozolium, N,N'-ethylmethylimidazolium, N,N'-butylmethylimidazolium or methyltriethylammonium cation. Preferably, the salt according to the invention is selected from the group constituting of N,N'-dimethylimidazolium methyl H-phosphonate, N,N'-butylmethylimidazolium methyl H-phosphonate, methyltriethylammonium methyl H-phosphonate, methyltributylammonium methyl H-phosphonate, N,N'-ethylmethylimidazolium ethyl H-phosphonate, N,N'-butylethylimidazolium ethyl H-phosphonate, and tetraethylammonium ethyl H-phosphonate, these salts being liquid at room temperature.

Within the scope of the present invention, stating that the radical R is unsaturated, means that it has at least one alkene or alkyne function. These liquid salts, according to the first alternative of the invention, may thus be advantageously used as a phosphorus-containing ionic liquid.

The object of the invention is therefore a phosphorus-containing ionic liquid consisting of the salt associating an ammonium cation with an alkyl H-phosphonate anion fitting formula I, wherein the radical R represents:

a $C_1$-$C_4$ hydrocarbon radical, or a $C_5$-$C_{14}$ hydrocarbon radical which is unsaturated and/or substituted with a function selected from the group constituting of ethers, esters, thioesters, and amides, the radicals $R_1$, $R_2$, $R_3$ and $R_4$ having the same definition as earlier.

The definitions of the functional substituents present on the $C_5$-$C_{14}$ hydrocarbon optionally unsaturated radical, are the same as earlier. Within the scope of the present invention, by ionic liquid is meant a salt consisting of an organic cation complexed with an inorganic or organic anion, which has the property of being in the liquid state at a temperature less than 100° C.

The ionic liquids according to the invention advantageously have the features of being:
non-volatile,
non-flammable,
stable at high temperature,
hydrophilic or amphiphilic,
good conductors.

The ionic liquids according to the invention will also be designated as RTILHPA, for "Room Temperature Ionic Liquids with H-Phosphonate Anions".

The radical $R_1$ advantageously represents a $C_1$-$C_6$ alkyl radical, more advantageously a methyl or ethyl radical. When the radical $R_4$ is present, the radicals $R_2$, $R_3$ and $R_4$ each advantageously represent independently of each other a $C_1$-$C_6$ alkyl radical, more particularly an ethyl, propyl or butyl radical. Otherwise, the radicals $R_3$ and $R_4$ may advantageously form together a pyrrolidine or morpholine radical and the radical $R_2$ represents a $C_1$-$C_6$ alkyl radical. When the radical $R_4$ is absent, the radicals $R_2$ and $R_3$ advantageously form together a pyridine or imidazole radical, optionally substituted with a $C_1$-$C_6$ alkyl chain.

Moreover, when the radical R represents a $C_5$-$C_{14}$ hydrocarbon radical, which is unsaturated and/or substituted with a function selected from the group consisting of ethers, ester, thioesters, and amides, the salts may have in addition to their use as an anionic liquid, other applications. For example, the amphiphilic character is enhanced, i.e. the corresponding salts are more soluble in organic solvents, which will facilitate dissolution of organic substances in synthesis. Additionally, the presence of functional groups on the chain may lead to task-specific ionic liquids similar to the functionalized imidazolium salts (cf. Functionalized imidazolium salts for task-specific ionic liquids and their applications, Sang-gi Lee, Chem. Commun., 2006, 1049).

Preferably, the ionic liquid is selected from the group consisting of N,N'-dimethylimidazolium methyl H-phosphonate, N,N'-butylmethylimidazolium methyl H-phosphonate, methyltriethylammonium methyl H-phosphonate, methyltributylammonium methyl H-phosphonate, N,N'-ethylmethylimidazolium ethyl H-phosphonate, N,N'-butylethylimidazolium ethyl H-phosphonate, and tetraethylammonium ethyl H-phosphonate. In a particular embodiment, the salt of the invention will not be N,N'-ethyl-methylimidazolium methyl H-phosphate.

The RTILHPAs according to the invention are room temperature liquids thermally stable (T>150° C.), easy to keep and which may be prepared in a large amount. They have the same solvent power as conventional room temperature ionic liquids (BMIM/$BF_4$, BMIM/$PF_6$, BMIM/dca, BMIM/N($SO_2CF_3$)$_2$...) used in synthesis, BMIM and dca respectively representing a N,N'-butylmethylimidazolium and a dicyanamide.

The viscosities of these RTILHPAs are remarkably low. Generally, they are less dense than conventional ionic liquids. They are excellent solvents of simple (amines, aldehydes, ketones, ...) or complex (metal catalysts, polyols, ...) organic compounds. They are miscible in protic solvents and immiscible in hydrocarbons.

Further, they have several advantages including those listed below. First of all, the RTILHPAs are excellent "reagent-solvents" for Heck and Suzuki coupling reactions. The Heck and Suzuki coupling reactions are one of the very performing methods for building an aryl carbon/carbon bond. But they require catalysts based on Pd(0): Pd nanoparticles, Pd (PPh$_3$)$_4$, Pd-carbene complexes ... or on Pd(II): Pd (OAc)$_2$, Pd(OAc)$_2$/PPh$_3$, adducts of N-heterocyclic Pd-carbenes, palladacycles ..., the preparation of which is sometimes laborious.

In the RTILHPAs, the salts of Pd(II): PdBr$_2$, PdSO$_4$, Pd(OAc)$_2$, prove to be excellent catalysts for coupling reactions (Heck and Suzuki) even in the absence of neutral ligands such as trialkylphosphines, dba, cod... Pd(II) is hot-reduced in situ by RTILHPA into active Pd(0), either as palladium black or as nanoparticles, or possibly as active Pd-carbene complexes. Additionally, these are solvents which do not contain any halide ions capable of poisoning the catalysts.

Comparatively to commercial ionic liquids, these RTILHPAs provide as reaction solvents, original potentialities. As an example, we shall mention the aldolization reaction between an aromatic aldehyde and acetone. In a conventional ionic liquid of the butylmethylimidzolium/PF$_6$ type, the scientific literature claims that hydroxylketone was obtained. Under the same experimental conditions, the use of RTILHPA quantitatively leads to the trans-enone. In many cases, this reaction is carried out at room temperature and with very short reaction times. Comparatively to the Claisen-Schmidt reaction which is highly used industrially, the experimental conditions are less drastic, more economical in energy and especially of very simple application with regeneration and therefore recycling of RTILHPA, which provides a real advantage during the industrial synthesis of enones.

For instance, applied to the self-aldol condensation of octanal, synthesis of 2-hexyl-2-decenal is obtained within 48 hrs at 25° C. with complete conversion of the initial aldehyde and 72% of formation of the C16 compound. These results remain unchanged after 3 reaction cycles with recovered RTILHPA. The simplicity and the regioselectivity of this reaction should raise interest in the industrial world of perfumes and flavourings. Thus, these RTILHPAs may be used as a specific solvent for aldolization reactions.

These RTILHPAs may also be used as solvents for polyols, such as monosaccharides or polysaccharides or cellulose. Indeed, polyols are relatively soluble in RTILHPAs with an ammonium cation, and in particular with an imidazolium cation. As an example, D-glucose and fir tree cellulose powder are soluble in N,N'-butylmethylimidazolium methyl H-phosphonate at a concentration of 100% by weight and more, and of about 10% by weight, respectively.

In particular, the RTILHPAs according to the invention may be an excellent solvent for solubilizing cellulose relatively to known ionic liquids: N,N'-butyl methyl imidazolium chloride (R. P. Swatloski et al., J. Am. Chem. Soc. 2002, 124, 4974-4975), N,N'-allyl methyl imidazolium chloride (H. Zhang et al. Macromolecules 2005, 38, 8272-8277), N,N'-dialkyl imidazolium formate (Y. Fukaya et al., Biomacromolecules, 2006, 7, 3295-3298). This dissolving power is of very high interest because cellulose which is a glucose polymer very abundant in nature, is soluble with difficulty in conventional solvents. Its solubilization in ionic liquids allows its physical transformations (fiber nature) and chemical transformations in order to access with lower costs, to novel compounds with various properties and many industrial applications (fabrics, paints, plastics, galenics, etc.). Once the transformation of cellulose has been carried out, the latter may be separated from the reaction medium by precipitation when water is added.

Also, the RTILHPAs according to the invention may be an excellent medium for acetylating sugars. Per-acetylation of oses (mono-, di-saccharides) with acetic anhydride is easily performed in RTILHPA solvents especially in solvents with a N,N'-dialkylimidazolium cation such as BMIM, DMIM (N,N'-butylmethylimidazolium and N,N'-dimethylimidazolium, respectively). The reaction often takes place around 50-60° C. and is completed within 12 hrs. It is likely that the acetylation agent is an acetyl H-phosphonate mixed anhydride, formed in situ, more active than acetic anhydride.

The object of the invention is therefore also the use of an ionic liquid according to the invention as a solvent, notably in organic synthesis and catalysis reactions, in particular in coupling reactions (Heck, Suzuki) and aldolization, and for solubilizing a polyol, such as a monosaccharide, a polysaccharide or cellulose. By "solubilization", is meant in the sense of the present invention that a compound, such as a polyol, may be solubilized in the ionic liquid at a concentration which may reach 10% by weight until a homogenous and limpid solution is obtained. This solubilization is carried out by stirring the mixture of the compound and of the ionic liquid at a temperature comprised between 25° C. and 100° C., preferably between 25° and 50° C., and in particular at room temperature, the complete solubilization of the compound generally being obtained within a period comprised between 1 hr and 6 hrs, this period being all the longer as the temperature of the mixture is low.

The ionic liquids according to the invention may in particular solubilize cellulose at a high concentration (up to 10% by weight). The RTILHPAs according to the invention may also be used as extraction solvents. For a binary system: RTILHPA-hydrophobic solvent or RTILHPA-polar solvent (acetone, ethyl acetate . . . ), the partition coefficient of an amine is always considerably larger in the ionic liquid (>70%). Tests performed with N-methylimidazole indicate that this base is preferably soluble in N,N'-dimethylimidazolium or N,N'-butylmethylimidazolium methyl H-phosphonate. RTILHPAs may therefore be used for storing amines. The object of the invention is also the use of an ionic liquid according to the invention, as a substitute for organic solvents in biphasic systems involved in separation and extraction systems.

RTILHPAs according to the invention may further be used as an additive for lubrication, this additive preventing decomposition of the lubricant by oxidation. An object of the invention is therefore also a lubrication composition comprising, in a majority amount, a lubricant (glycol polyoxyalkylene, glycol ether, . . . ) and, in a minority amount, a RTILHPA according to the invention and optionally other conventional additives.

The object of the invention is also the use of an ionic liquid according to the invention, as a solvent in the synthesis of nanostructured materials, such as nanoparticles. Moreover, RTILHPAs according to the invention are insoluble in most conventional organic solvents (ketones, ethers, hydrocarbons, chlorinated or fluorinated solvents . . . ). There are therefore easily recyclable. Further, their simple, fast synthesis for a moderate cost as well as their low viscosity and their physical properties make them ideal candidates for replacing solvents conventionally used in organic chemistry, within the scope of development of "green chemistry".

According to a second advantageous alternative of the invention, the salts of formula I according to the invention are pasty or solid, at room temperature. Generally, these salts are pasty or solid when the radical R represents a saturated $C_5$-$C_{14}$ hydrocarbon radical which is not substituted with functional groups. With a relatively high melting point (40° C.<mp<100° C.), these salts may be used as an ionic liquid, as an amphiphilic solvent for reactions which are carried out at high temperature.

Another object of the invention is a method for preparing a salt according to the invention for which $R_1$ represents a methyl or ethyl radical (a radical R' as defined below), comprising the reaction of a dialkylphosphite of formula II

wherein R has the same definition as for formula I and R' represents a methyl or ethyl radical
with a nitrogen-containing base fitting the following formula III

wherein $R_2$, $R_3$ and $R_4$ have the same definition as for the formula I, and then recovery of said ionic liquid.

The first preparation of monoalkyl H-phosphonates was described by Zwierzak et al. (*Tetrahedron* 1973, 29(8)), according to a two-step method from di-t-butylphosphite ((tbutylO)$_2$PHO). The phosphite is first transformed by hydrolysis into ammonium mono t-butyl H-phosphonate followed by alkylation with the corresponding alkyl halide and then by detbutylation. The products are isolated as S-(p-chlorobenzyl)thiouronium.

Monoalkyl H-phosphonates may also be obtained from diphenylphosphite by transesterification with an alcohol followed by ammonolysis (Kers A. et al., *Synthesis*, 1995, 427-430). Esterification of phosphorous acid $H_3PO_3$ also leading to monoalkylphosphites, has been reported (GB 1,302,894). The products were isolated as tertiary ammoniums ($HNR_3^+$).

Another industrial method (U.S. Pat. No. 4,143,059) for producing aluminium ethyl H-phosphonate, a fungicidal agent, was claimed. This is a reaction, the mechanism of which has not been elucidated, which consists of treating diethylphosphite with phosphorous acid leading to a mixture in which ethyl H-phosphonate is in majority (80-90%), which may be directly used in formulating fungicidal agents.

The mentioned methods are not suitable for preparing pure RTILHPAs and in a large amount. The method for preparing monoalkyloxy H-phosphonates according to the invention is simpler. It consists of dealkylating commercial dialkylphosphites in particular dimethylphosphite and diethylphosphite or methylated mixed phosphates.

A method for dealkylating dialkylphosphite with amines has already been described (Troev K. et al., Bull. Chem. Soc. Jpn, 1990, 63, 4, 1284-1280; FR 2 486 079). Nevertheless, this method as described in the literature, involves resorting to methanol as a solvent and to 100% molar excess of dialkylphosphite, the removal of which is not easy. Moreover, this type of method for dealkylation of dialkylphosphite with a tertiary morpholine, substituted with an alkyl chain containing from 8 to 50 carbon atoms, has also been described in U.S. Pat. No. 2,815,345. This method is however limited to the use of a base of the morpholine type.

One of the great advantages of the method according to the invention lies in the fact that the reaction step between dialkylphosphite and the nitrogen-containing base may be carried out in the absence of any solvent. One therefore has a preparation method respectful of the environment. In the method according to the invention, the molar ratios are advantageously from 1 to 3 moles, more advantageously 1.5 mole, of nitrogen-containing base of formula III for one mole of dialkylphosphite of formula II.

The salts may be obtained by a so-called thermal route method. According to this alternative, the reaction step between dialkylphosphite and the nitrogen-containing base is carried out at a temperature above 80° C., advantageously comprised between 80 and 120° C. The reaction step between dialkylphosphite and the nitrogen-containing base is advantageously carried out under an inert atmosphere, in particular under a nitrogen atmosphere. In particular, dealkylation (deethylation, de-methylation) of a neutral ester of H-phosphonates with a nucleophilic agent (nitrogen-containing base) such as N-alkylimidazole or trialkylamine, is carried at a high temperature (80-120° C.) for 24 to 48 hours. The obtained phosphorus-containing salt may then be easily purified, for example either by drying in a reduced vacuum at 110° C. or by extraction with a "water-chloroform" mixture followed by drying in vacuo of the aqueous phase.

According to an advantageous alternative of the method according to the invention, the salts are obtained by a so-called microwave irradiation method. According to this alternative, the reaction step between dialkylphosphite and the nitrogen-containing base is carried out by submitting the dialkylphosphite and nitrogen-containing base mixture to microwaves, per cycle in a domestic oven. With the technique of irradiation with microwaves, it is possible to considerably reduce the manufacturing time to about thirty minutes. Nevertheless, in order to avoid evaporation and degradation of the products under irradiations of long duration or at a too high power of the domestic oven, it requires preliminary adjustment depending on the amount of material used. For an amount of material used varying from 10 to 30 g, a cycle advantageously comprises 30-60 seconds of irradiation at a power comprised between 100 and 180 Watts followed by cooling to room temperature. The cycle is advantageously repeated for 30-60 times.

Taking into account the preparation method in a single step without using any organic solvent, the availability and the low cost of the raw materials (dialkylphosphites, N-alkylimidazoles, trialkylamines), the method for making the salts and thus novel phosphorus-containing ionic liquids, is less expensive and "greener" than those of known conventional ionic liquids, the obtaining of which has to go through two steps and resort to metathesis from ammonium (N,N'-dialkylimidazoliums, quaternary ammoniums, phosphoniums) halide salts with fluorinated anions such as $NaBF_4$, $HPF_6$, $LiN(SO_2CF_3)_2$ or from a silver salt (Ag/dca for example).

Methylated mixed phosphites may be obtained by known methods, for example:
synthesis from $PCl_3$ and the corresponding alcohol by the method of Ford-Moore et al., Org. Syn. Coll. Vol. IV p. 955 or the method of Cook et al., J. Chem. Soc. 635, (1949), (this method only gives symmetrical phosphites), by adding $PCl_3$ to a corresponding alcohol/water mixture and then distillation, according to the method described in U.S. Pat. No. 4,045,519, and, for dialkylphosphites having two different alkyl radicals, by the method described in patent DE 1,078,558.

They may also be obtained by the novel method, also object of the invention, developed by the inventors. This novel method involves transesterification of dimethylphosphite, a commercial product with a heavy alcohol in the presence of a catalyst. The catalyst is advantageously a tertiary amine, more advantageously triethylamine. Other amine bases may also be used as a catalyst. Thus, it is possible to use tributylamine (0.5 equivalents), DBU: (Diaza(1,3)bicyclo[5.4.0]undecane) (0.2 equivalents). Because of its low boiling point, triethylamine is preferred (purification of mixed phosphites then being easier).

According to a preferred embodiment, dimethylphosphite (4 equivalents) is treated at room temperature with an alcohol ROH in the presence of triethylamine (1 equivalent) in order to lead to the mixed phosphite. The molar ratios are advantageously from 1 to 10 equivalents, more advantageously 4 equivalents, of dimethylphosphite for 1 equivalent of triethylamine. The group R of the alcohol ROH is a $C_1$-$C_{14}$, advantageously $C_5$-$C_{14}$, hydrocarbon radical. The alcohols having more than 8 carbon atoms give better yields.

In the presence of the preferred catalyst (triethylamine), the reaction may be written as:

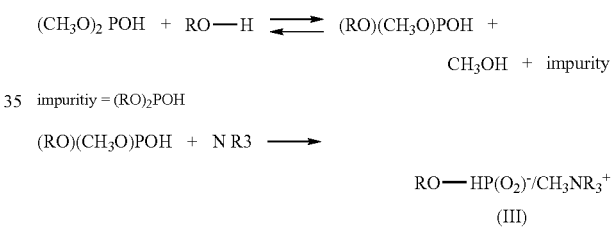

$$(CH_3O)_2POH + RO\text{---}H \rightleftharpoons (RO)(CH_3O)POH +$$
$$CH_3OH + \text{impurity}$$
$$\text{impuritiy} = (RO)_2POH$$
$$(RO)(CH_3O)POH + NR3 \longrightarrow$$
$$RO\text{---}HP(O_2)^-/CH_3NR_3^+$$
(III)

This method gives the possibility of leading to a large number of methylated mixed phosphites. In particular, it is possible to synthesize methylated mixed phosphites having an alkyl radical comprising more than 4 carbon atoms, while the methods of the prior art were often limited to alkyl substituents comprising no more than 4 carbon atoms.

DETAILED DESCRIPTION

The following examples show potentialities of these liquid salts as solvents in synthesis through the universal and significant reactions in organic chemistry such as aldolization, Heck, Suzuki coupling reactions and a solvent "per excellence" of polysaccharides. The following examples illustrate the object of the present invention and are not limiting.

Example 1

Preparation of N,N'-Dimethylimidazolium Methyl H-Phosphonate or Methoxy Phosphonate a—By a Thermal Route A solution of dimethylphosphite (11.2 g, 0.1 mol) and of N-methylimidazole (9.85 g, 0.12 mol) is brought to 80° C. under a nitrogen atmosphere for 24 hrs. The solution is dried at 60° C. under reduced vacuum ($10^{-1}$ mmHg). The traces of N-methylimidazole may be eliminated by a water/chloroform extraction; the aqueous phase dried under reduced vacuum, at 60° C., gives a brassy yellow liquid (m=18.7 g; yield=97%).

Anal. calc. for $C_6H_{13}N_2O_3$: C, 37.50; H, 6.82; N, 14.57; theor.: C, 36.90; H, 6.88; N, 14.49;

$^1$H NMR (CD$_3$OD): δ 3.47 (d, 12 Hz, 3H); 3.90 (s, 6H); 6.63 (d, 608 Hz, 1H); 7.55 (s, 2H); 8.91 (s, 1H); $^{31}$P NMR (CD$_3$OD): +5.59 b—By Microwave Irradiation

A mixture of dimethylphosphite (5.5 g, 0.05 mol) and of N-methylimidazole (5 g; 0.06 mmol) is submitted to microwaves per cycle; 30 seconds of irradiation at 180 Watts followed by fast cooling to room temperature. The irradiation-cooling cycle is repeated 20 times; the excess of N-methylimidazole is removed at 60° C. under reduced vacuum; a brassy yellow oil is obtained (m=9.1 g, yield=95%).

Example 2

Preparation of N,N'-Butylmethylimidazolium Methyl H-Phosphonate or Methoxy Phosphonate A solution of dimethylphosphite (11.2 g, 0.1 mol) and of N-butylimidazole (16.08 g; 0.12 mol) is brought to 90° C. under a nitrogen atmosphere for 30 hrs. The solution is dried at 60° C. under reduced vacuum (10$^{-1}$ mmHg). The traces of N-butylimidazole are eliminated by extraction with <<water/chloroform>>; the aqueous phase dried under reduced vacuum at 80° C., gives a yellow liquid (m=15.6 g; yield=87%).

Anal. calc. for $C_9H_{19}N_2O_3P$: C, 46.15; H, 8.18; N, 11.96; theor.: C, 45.10; H, 8.21; N, 11.57;

$^1$H NMR (CD$_3$OD): δ 0.94 (t, 3H); 1.34 (m, 2H); 1.85 (m, 2H); 3.48 (d, 12 Hz, 3H); 3.93 (s, 6H); 4.23 (m, 2H); 6.62 (d, 608 Hz, 1H); 7.63-7.70 (m, 2H); 9.14 (s, 1H); $^{31}$P NMR (CD$_3$OD): +5.92

Example 3

Preparation of Triethylmethylammonium Methyl H-Phosphonate or Methoxy Phosphonate A solution of dimethylphosphite (11.2 g, 0.1 mol) and of triethylamine (20.2 g; 0.2 mol) is brought to 80° C. under a nitrogen atmosphere for 36 hrs. Two phases are formed. The recovered lower phase, dried at 60° C. under reduced vacuum (10$^{-1}$ mmHg) gives a brassy yellow liquid (m=12.5 g; yield=68%).

Anal. calc. for $C_8H_{22}NO_3P$: C, 45.49; H, 10.51; N, 6.63; theor.: C, 43.47; H, 10.51; N, 6.67;

$^1$H NMR (CDCl$_3$): δ 0.86 (t, 9H); 2.65 (s, 3H); 3.01 (q, 6H); 3.03 (d, 12 Hz, 3H); 6.29 (d, 588 Hz, 1H); $^{31}$P NMR (CD$_3$OD): +4.65

Example 4

Preparation of Tributylmethylammonium Methyl H-Phosphonate or Methoxy Phosphonate A solution of dimethylphosphite (11.2 g, 0.1 mol) and of tributylamine (45.5 g; 0.2 mol) is brought to 120° C. under a nitrogen atmosphere for 36 hrs. Two phases are formed. The recovered lower phase, dried at 80° C. under reduced vacuum (10$^{-1}$ mmHg) gives a very viscous yellow liquid (m=22.5 g; yield=66%).

Anal. calc. for $C_{14}H_{34}NO_3P$: C, 49.40; H, 10.00; N, 4.12; theor.: C, 49.47; H, 10.21; N, 3.97;

$^1$H NMR (CDCl$_3$): δ 0.61 (t, 9H); 1.05 (m, 6H); 1.29 (m, 6H); 2.82 (s, 3H); 2.99 (m, 6H); 3.11 (d, 12 Hz, 3H); 6.42 (d, 594 Hz, 1H); $^{31}$P NMR (CDCl$_3$): +5.14

Example 5

Preparation of N,N'-Ethylmethylimidazolium Ethyl H-Phosphonate or Ethoxy Phosphonate A solution of diethylphosphite (11.2 g, 0.1 mol) and of N-methylimidazole (16.4 g; 0.2 mol) is brought to 100° C. under a nitrogen atmosphere for 36 hrs. The solution is dried at 60° C. under reduced vacuum (10$^{-1}$ mmHg). The traces of N-methylimidazole are eliminated by extraction with <<water/chloroform>>; the aqueous phase dried under reduced vacuum at 60° C., gives a brassy yellow liquid (m=15.9 g; yield=72%).

Anal. calc. for $C_8H_{17}N_2O_3P$: C, 45.47; H, 8.58; N, 13.25; theor.: C, 44.98; H, 8.48; N, 13.40;

$^1$H NMR (D$_2$O): δ 1.11 (t, 3H); 1.37 (t, 3H); 3.77 (dq, 7.3 Hz, 2H); 3.77 (s, 3H); 4.11 (q, 7.15 Hz, 2H); 6.56 (d, 633 Hz, 1H); $^{31}$P NMR (D$_2$O): +5.85

Example 6

Preparation of N,N'-Butylethylimidazolium Ethyl H-Phosphonate or Ethoxy Phosphonate A solution of diethylphosphite (11.2 g, 0.1 mol) and of N-butylimidazole (24.8 g; 0.2 mol) is brought to 100° C. under a nitrogen atmosphere for 48 hrs. The solution is dried at 60° C. under reduced vacuum (10$^{-1}$ mmHg). The traces of N-methylimidazole are eliminated by extraction with "water/chloroform"; the aqueous phase dried under reduced vacuum at 60° C., gives a yellow liquid (m=15.5 g; yield=63%).

Anal. calc. for $C_{11}H_{23}N_2O_3P$: C, 53.65; H, 9.35; N, 11.38; theor.: C, 54.98; H, 9.48; N, 11.40;

$^1$H NMR (CDCl$_3$): δ 0.61 (t, 3H); 0.90 (t, 3H); 1.30 (m, 2H); 1.55 (m, 2H); 3.58 (m, 2H); 3.97 (t, 2H); 4.04 (q, 2H); 6.57 (d, 600 Hz, 1H); 7.21-7.33 (m, 2H); 10.13 (s, 1H); $^{31}$P NMR (CDCl$_3$): +3.44

Example 7

Preparation of Tetraethylammonium Ethyl H-Phosphonate or Ethoxy Phosphonate

A solution of diethylphosphite (11.2 g, 0.1 mol) and of triethylamine (30.3 g; 0.3 mol) is brought to 120° C. under a nitrogen atmosphere for 48 hrs. Two phases are formed. The recovered lower phase dried at 60° C. under reduced vacuum (10$^{-1}$ mmHg) gives a yellowish liquid (m=10.5 g; yield=50%).

Anal. calc. for $C_{10}H_{26}NO_3P$: C, 50.19; H, 10.08; N, 5.86; theor.: C, 49.99; H, 8.90; N, 5.92;

$^1$H NMR (CDCl$_3$): δ 0.98 (t, 9H); 1.11 (s, 12H); 3.18 (q, 8H); 3.66 (dq, 2H); 6.54 (d, 618 Hz, 1H); $^{31}$P NMR (CDCl$_3$): +6.80

Example 8

Preparation of N,N'-Dimethylimidazolium Octyl H-Phosphonate or Octoxyphosphonate or Octyloxyphosphonate Methyloctylphosphite (1.04 g, 5 mmol) is treated with N-methylimidazole (0.82 g; 10 mmol) at 80° C. until complete disappearance of the mixed phosphite (by TLC). N-methylimidazole is driven out under reduced vacuum ($10^{-1}$ mmHg). A residue is dissolved in water (5 mL) and washed with hexane (3×5 mL). After driving out water under reduced vacuum at 60° C., a pasty product is obtained (m=1.1 g; 71%).

Anal. calc. for $C_{13}H_{27}N_2O_3P$: C, 54.55; H, 9.44; N, 8.39; theor.: C, 54.22; H, 9.26; N, 8.54;

$^1H$ NMR (CDCl$_3$): δ 0.66 (t, 3H); 1.05 (m, 2H); 1.40 (m, 2H); 3.62 (t, 2H); 3.83 (s, 6H); 6.72 (d, 597 Hz, 1H); 7.32 (s, 2H); 10.25 (s, 1H)

By following these different operating modes (Examples 1-8), the following salts (Table 1) were prepared:

TABLE 1 salts according to the invention

| RTILHP | | Yield | Viscosity (Pa · s) | | Density |
|---|---|---|---|---|---|
| Anion | Cation | % | 20° C. | 25° C. | 20° C. |
| CH$_3$O—PH(O)O$^-$ | DMIM$^+$ | 97 | 0.0654 | 0.0503 | 1.180 |
| CH$_3$O—PH(O)O$^-$ | BMIM$^+$ | 78 | 0.2963 | 0.2053 | 1.133 |
| CH$_3$O—PH(O)O$^-$ | CH$_3$NEt$_3^+$ | 72 | 0.1086 | 0.0826 | 1.107 |
| CH$_3$O—PH(O)O$^-$ | CH$_3$NBu$_3^+$ | 70 | nd | nd | nd |
| C$_2$H$_5$O—PH(O)O$^-$ | EMIM$^+$ | 72 | 0.1962 | 0.1400 | 1.134 |
| C$_2$H$_5$O—PH(O)O$^-$ | BEMIM$^+$ | 63 | 0.1269 | 0.0972 | 1.073 |
| C$_2$H$_5$O—PH(O)O$^-$ | Et$_4$N$^+$ | 50 | nd | nd | nd |
| nC$_6$H$_{13}$O—PH(O)O$^-$ | DMIM$^+$ | 35 | solid | solid | solid |
| nC$_8$H$_{17}$O—PH(O)O$^-$ | DMIM$^+$ | 42 | solid | solid | solid |
| nC$_{14}$H$_{29}$O—PH(O)O$^-$ | DMIM$^+$ | 40 | solid | solid | solid |

DMIM: N,N'-dimethylimidazolium
BMIM: N,N'-butylmethylimidazolium
EMIM: N,N'-ethylmethylimidazolium
BEMIM: N,N'-butylethylimidazolium
nd: not determined Example 9

Preparation of Hexyl Methylphosphite

A mixture of dimethylphosphite (22 g, 0.20 mol), hexanol (5.1 g; 0.05 mol) and triethylamine (5.05 g; 0.05 mol) is stirred at room temperature. The reaction is followed with TLC until disappearance of hexanol. Triethylamine is driven out under vacuum with in the evaporator, the mixed phosphite is extracted with hexane (3×25 mL). The organic phase is washed with water (3×10 mL) and dried on anhydrous Na$_2$SO$_4$. Evaporation in vacuo gives a colorless liquid (m=5.40 g; 60%) which contains 95% of mixed phosphite (as determined by $^{31}$P NMR). The mixed phosphite is directly used in the dimethylation by N-methylimidazole without any preliminary purification.

An alternative for recovering the excess dimethylphosphite:

Once the reaction is completed, the triethylamine driven out with the rotary evaporator, the hexane extract submitted to distillation under reduced vacuum ($10^{-1}$ mmHg) at 60° C. allows the excess dimethylphosphite to be recovered. The mixed phosphite is used as such in the demethylation step.

$^1H$ NMR (300 MHz, CDCl$_3$): δ 0.80 (t, 3H); 1.18 (s, 8H); 1.62 (m, 2H); 1.68 (d, 12 Hz, 3H); 3.99 (m, 2H); 6.7 (d, 693 Hz, 1H); $^{31}$P NMR (121.5 MHz, CDCl$_3$): 8.82 ppm By following the same operating mode, octylmethylphosphite and tetradecylmethylphosphite were prepared.

Octyl methylphosphite: colorless oil, 75%; $^1H$ NMR (CDCl$_3$): δ 0.80 (t, 3H); 1.19 (s, 10H); 1.64 (m, 2H); 3.69 (d, 12 Hz, 3H); 3.98 (m, 2H); 6.7 (d, 693 Hz, 1H); $^{31}$P NMR (CDCl$_3$): +9.15 ppm Tetradecylmethylphosphite: colorless oil, 100%; $^1H$ NMR (300 MHz, CDCl$_3$): δ 0.79 (t, 3H); 1.17 (s, 22H); 1.61 (m, 2H); 3.68 (d, 12 Hz, 3H); 3.99 (m, 2H); 6.7 (d, 693 Hz, 1H); $^{31}$P NMR (CDCl$_3$): +9.22 ppm Example 10

Heck Coupling Reaction: Preparation of Stilbene

A solution of iodobenzene (1 mmol), of styrene (1.5 mmol), of PdBr$_2$ or PdSO$_4$ (10 mol %) and of triethylamine (2 mmol) in N,N'-butylmethylimidazolium methyl H-phosphonate (2 g) is brought to 110° C. for 5 hrs. The formed trans-stilbene is extracted with ether (3×10 mL), the structure of which is confirmed by $^1H$ NMR. (yield=100%).

Note: the recovered RTILHPA-Pd mixture, dried in vacuo may be recycled several times for the same type of reaction.

Example 11

Suzuki Coupling Reaction: Preparation of 1-Phenylnaphthalene

A solution of bromobenzene (1 mmol), of 1-naphthylboronic acid (1.2 mmol), of PdBr$_2$ (2.5 mol %), and of triethylamine (2 mmol) in N,N'-butylmethylimidazolium methyl H-phosphonate of (1 g) is brought to 100° C. under stirring for 24 hrs. Extraction with hexane (3×5 mL) gives a white and sublimable solid (Mp 112-113° C.), (m=0.2 g; yield=98%).

Example 12

Preparation of 4-(4-bromophenyl)but-3-en-2-one

The p-bromobenzaldehyde (1 mmol) and the L-proline (30 mol %) are dissolved in N,N'-dimethylimidazolium methyl H-phosphonate (1 ml). The acetone (1 ml) is added. The mixture is stirred at room temperature until disappearance of the bromobenzaldehyde (followed by Thin Layer Chromatography). 4-(4-bromophenyl)but-3-en-2-one is isolated by extraction with ether (3×5 ml). The product is purified by column chromatography (0.96 g; yield=80%).

$^1H$ NMR (CDCl$_3$): δ 2.28 (s, 3H); 6.55 (d, 16 Hz, 1H); 7.33 (d, 1H); 7.40 (d, 1H); 7.39-7.42 (m, 4H).

The same product is obtained by following the same operating procedure but by replacing L-proline with glycine or valine.

Example 13

Per-Acetylation of a Monosaccharide: Preparation of Glucose Penta-Acetate

A solution of D-glucose (0.36 g; 2 mmol) in N,N'-dimethylimidazolium or N,N'-butylmethyl methyl H-phosphonate (1 g) is treated with acetic anhydride (1.02 g; 10 mmol) at room temperature under stirring. The reaction is exothermic; the mixture becomes homogeneous. After 15 hrs at room temperature or 5 hrs at 50° C., glucose penta-acetate is precipitated by adding water (m=0.72 g; yield=92%).

Example 14

Per-Acetylation of a Disaccharide: Preparation of Lactose Octaacetate

A solution of D-lactose monohydrate (0.36 g; 1 mmol) in N,N'-dimethylimidazolium methyl H-phosphonate (1 g) is treated with acetic anhydride (0.92 g; 9 mmol) at room temperature under stirring for 15 min. The solution is then brought to 60° C. for 8 hours. The peracetylated lactose is extracted with a <<water-chloroform>> mixture. The chloroform phase evaporated in vacuo gives a white solid (m=0.53 g; yield=83%).

Example 15

Solubilization of Cellulose with a DP of 2,000 up to 20% by Weight

To 5 g of cellulose with an average degree of polymerization (DP) of 2,000 g/mol, are added 20 g of ionic liquid: N,N'-dimethylimidazolium methyl H-phosphonate.

After 10 minutes of stirring at 50° C., the cellulose is dissolved (at 20% by weight based on the total weight of cellulose/ionic liquid mixture) and forms a homogeneous transparent gel with the ionic liquid.

At 6% by weight of cellulose (based on the total weight of cellulose/ionic liquid mixture), a liquid mixture and not a gel is obtained.

The dissolution of cellulose was also carried out at 25° C. in the same cellulose/ionic liquid proportions (5 g of cellulose for 20 g of ionic liquid). The same result was obtained after 30 minutes of stirring.

Example 16

Solubilization of Powdered 10 wt % Fir Tree Cellulose

To 0.5 g of powdered fir tree cellulose placed in a test-tube, are added 5 g of N,N'-butylmethylimidazolium methyl H-phosphonate. The mixture is stirred at 50° C. for two hours. A limpid and viscous solution is obtained.

Addition of water causes precipitation of cellulose.

The invention claimed is:

1. A method for reducing the use of organic solvent comprising substituting an organic solvent with an ionic liquid comprising a salt associating an ammonium cation with an alkyl H-phosphonate anion fitting the following formula I:

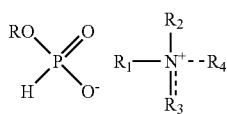

wherein
R represents a saturated or unsaturated C1-C14 hydrocarbon radical, optionally substituted with a function selected from the group consisting of ethers, esters, thioesters and amides;
R1 represents a C1-C6 hydrocarbon radical;
the bond in dotted lines may either be present or not, the radical R4 then being present or absent,
  if the radical R4 is present, the bond with R3 is a single bond, and
R2, R3 and R4 represent independently of each other a C1-C6 hydrocarbon radical or
R3 and R4 form together a heterocycloalkyl radical with 5 or 6 members, the heterocycloalkyl radical may have in addition to the nitrogen atom which bears them, one or more hetero-atoms selected from N and O, the heterocycloalkyl radical may be substituted with one or more C1-C6 alkyl radicals and R2 represents a C1-C6 hydrocarbon radical,
if the radical R4 is absent, the bond with R3 is a double bond, and R2 and R3 form together a heteroaromatic radical with 5 or 6 members, the heteroaromatic radical may have, in addition to the nitrogen atom which bears them, one or more hetero-atoms selected from N and O, the heteroaromatic radical may be substituted with one or more C1-C6 alkyl radicals.

2. The method according to claim 1, wherein the radical $R_1$ represents a $C_1$-$C_6$ alkyl radical.

3. The method according to claim 1, wherein the radical $R_4$ is present and the radicals $R_2$, $R_3$ and $R_4$ each represent independently of each other, a $C_1$-$C_6$ alkyl radical.

4. The method according to claim 1, wherein the radical $R_4$ is present, the radicals $R_3$ and $R_4$ form together a pyrrolidine or morpholine radical and the radical $R_2$ represents a $C_1$-$C_6$ alkyl radical.

5. The method according to claim 1, wherein the radical $R_4$ is absent and the radicals $R_2$ and $R_3$ form together a pyridine or imidazole radical optionally substituted with a $C_1$-$C_6$ alkyl chain.

6. The method according to claim 1, further comprising selecting the salt from the group consisting of N,N'-dimethylimidazolium methyl H-phosphonate, N,N'-butylmethylimidazolium methyl H-phosphonate, methyltriethylammonium methyl H-phosphonate, methyltributylammonium methyl H-phosphonate, N,N'-ethylmethyl-imidazolium ethyl H-phosphonate, N,N'-butylethylimidazolium ethyl H-phosphonate, tetraethylammonium ethyl H-phosphonate, N,N'-dimethylimidazolium n-butyl H-phosphonate, N,N'-dimethyl-imidazolium n-hexyl H-phosphonate, N,N'-dimethylimidazolium n-octyl H-phosphonate and N,N'-dimethylimidazolium tetradecyl H-phosphonate.

7. The method according to claim 1, wherein the salt is liquid at a temperature below 100° C.

8. The method according to claim 7, wherein the salt is liquid at room temperature.

9. The method according to claim 7, wherein the radical R represents a $C_1$-$C_4$ hydrocarbon radical.

10. The method according to claim 7, wherein the radical R represents a $C_5$-$C_{14}$ hydrocarbon radical which is unsaturated and/or substituted with a function selected from the group consisting of ethers, esters, thioesters and amides.

11. The method according to claim 7, further comprising selecting the salt from the group consisting of N,N'-dimethylimidazolium methyl H-phosphonate, N,N'-butylmethylimidazolium methyl H-phosphonate, methyltriethylammonium methyl H-phosphonate, methyltributylammonium methyl H-phosphonate, N,N'-ethylmethylimidazolium ethyl H-phosphonate, N,N'-butylethylimidazolium ethyl H-phosphonate, and tetraethylammonium ethyl H-phosphonate.

12. The method according to claim 1, further comprising selecting the ionic liquid as a solvent.

13. The method according to claim 12, further comprising selecting the ionic liquid for solubilizing a polyol.

14. The method according to claim 1, further comprising selecting the ionic liquid as a substitute for organic solvents in biphasic systems involved in separation and extraction systems.

15. The method according to claim 2, wherein the radial $R_1$ represents a methyl or ethyl radical.

16. The method according to claim 9, wherein the radical R represents a methyl or ethyl radical.

17. The method according to claim 13, wherein the polyol is a monosaccharide, a polysaccharide or cellulose.

* * * * *